(12) United States Patent
Shaw et al.

(10) Patent No.: US 7,279,002 B2
(45) Date of Patent: Oct. 9, 2007

(54) CUTTING STENT AND BALLOON

(75) Inventors: William J. Shaw, Cambridge, MA (US); Eric B. Stenzel, Galway (IE); Lixiao Wang, Long Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 646 days.

(21) Appl. No.: 10/423,598

(22) Filed: Apr. 25, 2003

(65) Prior Publication Data

US 2004/0215223 A1   Oct. 28, 2004

(51) Int. Cl.
*A61F 2/06*   (2006.01)
*A61M 29/00*   (2006.01)

(52) U.S. Cl. .................... 623/1.11; 606/159
(58) Field of Classification Search ............. 606/159, 606/108, 194; 623/1.11, 1.12
See application file for complete search history.

(56) References Cited

U.S. PATENT DOCUMENTS

| | | | |
|---|---|---|---|
| 4,273,128 A | 6/1981 | Lary | 606/159 |
| 4,669,469 A | 6/1987 | Gifford, III | 606/159 |
| 4,696,667 A | 9/1987 | Masch | 604/22 |
| 4,728,319 A | 3/1988 | Masch | 604/22 |
| 4,781,186 A | 11/1988 | Simpson et al. | 606/171 |
| 4,784,636 A | 11/1988 | Rydell | 604/22 |
| 4,787,388 A | 11/1988 | Hofmann | 128/344 |
| 4,867,157 A | 9/1989 | McGurk-Burleson et al. | 606/170 |
| 4,886,061 A | 12/1989 | Fischell et al. | 606/159 |
| 4,887,613 A | 12/1989 | Farr et al. | 606/159 |
| 4,896,669 A | 1/1990 | Bhate et al. | 606/194 |
| 4,909,781 A | 3/1990 | Husted | 604/22 |
| 4,950,277 A | 8/1990 | Farr | 606/159 |
| 4,963,313 A | 10/1990 | Noddin et al. | 264/573 |
| 4,966,604 A | 10/1990 | Reiss | 606/159 |
| 4,979,951 A | 12/1990 | Simpson | 606/159 |
| 4,986,807 A | 1/1991 | Farr | 604/22 |
| 5,030,201 A | 7/1991 | Palestrant | 604/22 |
| 5,053,044 A | 10/1991 | Mueller et al. | 606/159 |
| 5,074,871 A | 12/1991 | Groshong | 606/170 |
| 5,091,205 A | 2/1992 | Fan | 427/2 |
| 5,100,425 A | 3/1992 | Fischell et al. | 606/159 |
| 5,112,900 A | 5/1992 | Buddenhagen | 524/484 |
| 5,156,610 A | 10/1992 | Reger | 606/159 |
| 5,176,693 A | 1/1993 | Pannek, Jr. | 606/159 |
| 5,178,625 A | 1/1993 | Groshong | 606/159 |
| 5,181,920 A | 1/1993 | Mueller et al. | 606/159 |
| 5,192,291 A | 3/1993 | Pannek, Jr. | 606/159 |

(Continued)

FOREIGN PATENT DOCUMENTS

EP    0 565 799 B1    11/1992

(Continued)

OTHER PUBLICATIONS

U.S. Appl. No. 09/696,378, filed Oct. 25, 2000, Chen et al.

*Primary Examiner*—Anhtuan T. Nguyen
*Assistant Examiner*—Elizabeth Houston
(74) *Attorney, Agent, or Firm*—Vidas, Arrett & Steinkraus, P.A.

(57) ABSTRACT

A stent or sheath having one or more cutting blades may be constructed for implantation in the body. A balloon having one or more cutting blades may be used with a stent or a sheath.

4 Claims, 33 Drawing Sheets

U.S. PATENT DOCUMENTS

| | | | |
|---|---|---|---|
| 5,196,024 A * | 3/1993 | Barath | 606/159 |
| 5,224,945 A | 7/1993 | Pannek, Jr. | 606/159 |
| 5,226,887 A | 7/1993 | Farr et al. | 604/103.09 |
| 5,226,909 A | 7/1993 | Evans et al. | 606/159 |
| 5,250,059 A | 10/1993 | Andreas et al. | 606/159 |
| 5,282,484 A | 2/1994 | Reger | 128/898 |
| 5,320,634 A | 6/1994 | Vigil et al. | 606/159 |
| 5,372,601 A | 12/1994 | Lary | 606/159 |
| 5,447,497 A | 9/1995 | Sogard et al. | 604/101.02 |
| 5,527,325 A | 6/1996 | Conley et al. | 606/159 |
| 5,556,408 A | 9/1996 | Farhat | 606/180 |
| 5,616,149 A | 4/1997 | Barath | 606/159 |
| 5,669,920 A | 9/1997 | Conley et al. | 606/159 |
| 5,697,944 A | 12/1997 | Lary | 606/159 |
| 5,713,913 A | 2/1998 | Lary et al. | 606/159 |
| 5,718,684 A | 2/1998 | Gupta | 604/103.07 |
| 5,728,123 A | 3/1998 | Lamelson et al. | 604/22 |
| 5,746,716 A * | 5/1998 | Vigil et al. | 604/97.01 |
| 5,766,203 A | 6/1998 | Imran et al. | 623/1.11 |
| 5,792,158 A | 8/1998 | Lary | 606/159 |
| 5,797,935 A | 8/1998 | Barath | 606/159 |
| 5,800,450 A | 9/1998 | Lary et al. | 606/180 |
| 5,833,657 A | 11/1998 | Reinhardt et al. | 604/96 |
| 5,919,200 A | 7/1999 | Stambaugh et al. | 606/159 |
| 6,001,112 A | 12/1999 | Taylor | 606/159 |
| 6,036,708 A | 3/2000 | Sciver | 606/159 |
| 6,117,153 A | 9/2000 | Lary et al. | 606/170 |
| 6,165,187 A | 12/2000 | Reger | 606/159 |
| 6,197,013 B1 * | 3/2001 | Reed et al. | 604/509 |
| 6,258,108 B1 | 7/2001 | Lary | 606/159 |
| 6,306,151 B1 * | 10/2001 | Lary | 606/159 |
| 6,416,523 B1 | 7/2002 | Lafontaine | 606/159 |
| 6,428,552 B1 | 8/2002 | Sparks | 606/159 |
| 6,517,514 B1 | 2/2003 | Campbell | 604/96.01 |
| 6,562,062 B2 | 5/2003 | Jenusaitis et al. | 623/1.11 |
| 6,565,527 B1 | 5/2003 | Jonkman et al. | 604/96.01 |
| 6,632,231 B2 | 10/2003 | Radisch, Jr. | 606/159 |
| 6,685,718 B1 | 2/2004 | Wyzgala et al. | 606/170 |
| 6,730,105 B2 | 5/2004 | Shiber | 606/159 |
| 6,808,518 B2 * | 10/2004 | Wellman et al. | 604/507 |
| 2002/0010489 A1 * | 1/2002 | Grayzel et al. | 606/194 |
| 2002/0151924 A1 | 10/2002 | Shiber | 606/194 |
| 2003/0144677 A1 | 7/2003 | Lary | 606/159 |
| 2003/0163148 A1 | 8/2003 | Wang et al. | 606/159 |
| 2004/0122457 A1 | 6/2004 | Weber | 606/159 |
| 2004/0127920 A1 | 7/2004 | Radisch, Jr. | 606/159 |
| 2004/0133223 A1 * | 7/2004 | Weber | 606/159 |

FOREIGN PATENT DOCUMENTS

| | | |
|---|---|---|
| WO | 01/87372 | 11/2001 |

* cited by examiner

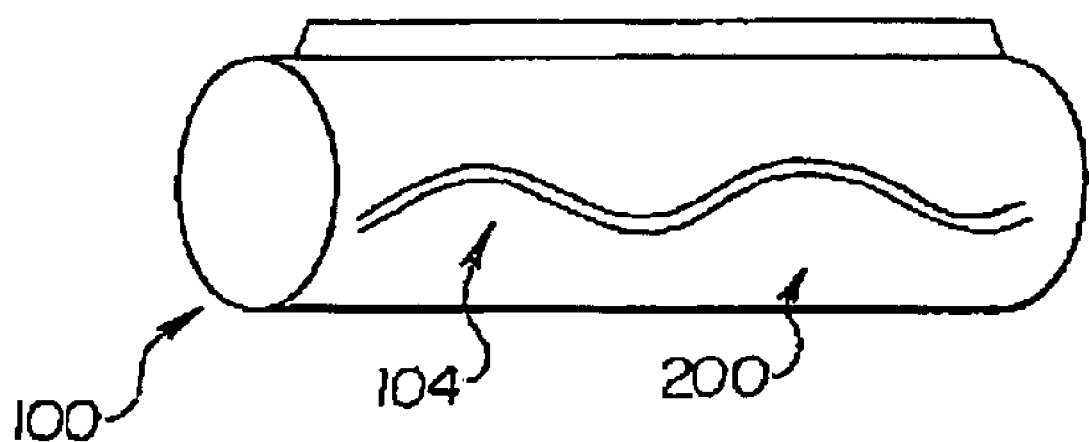

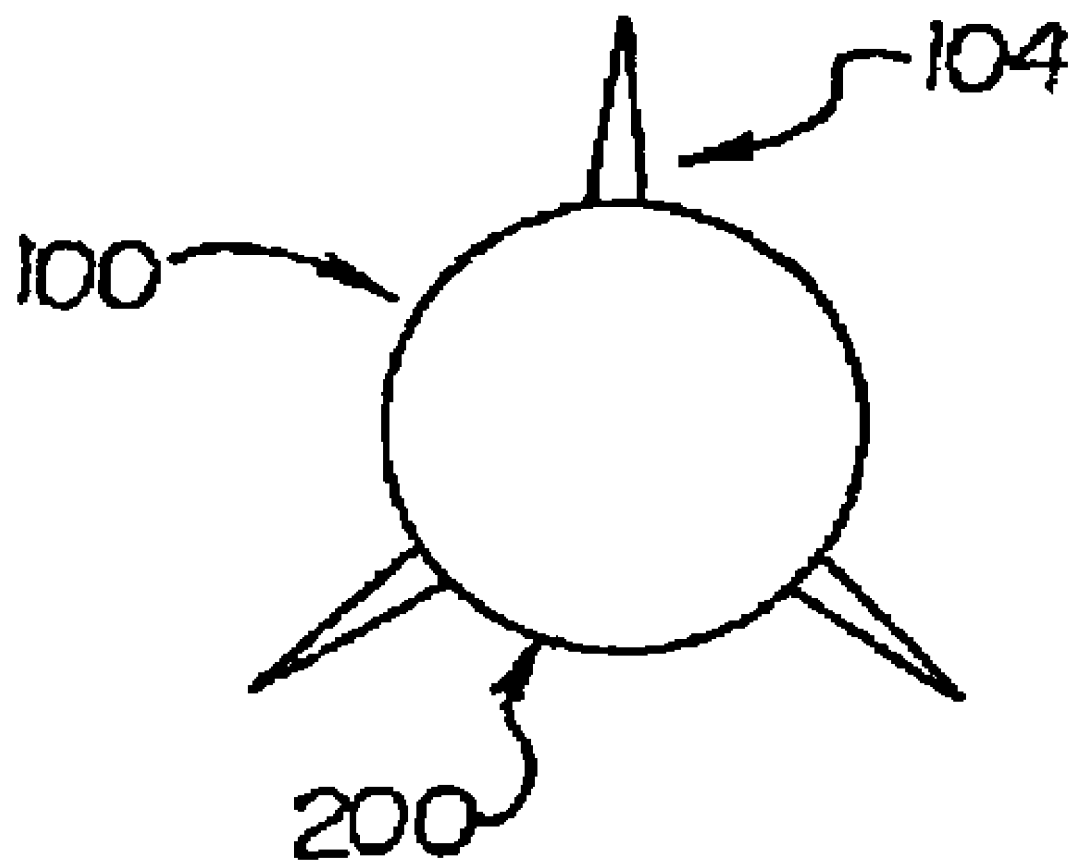

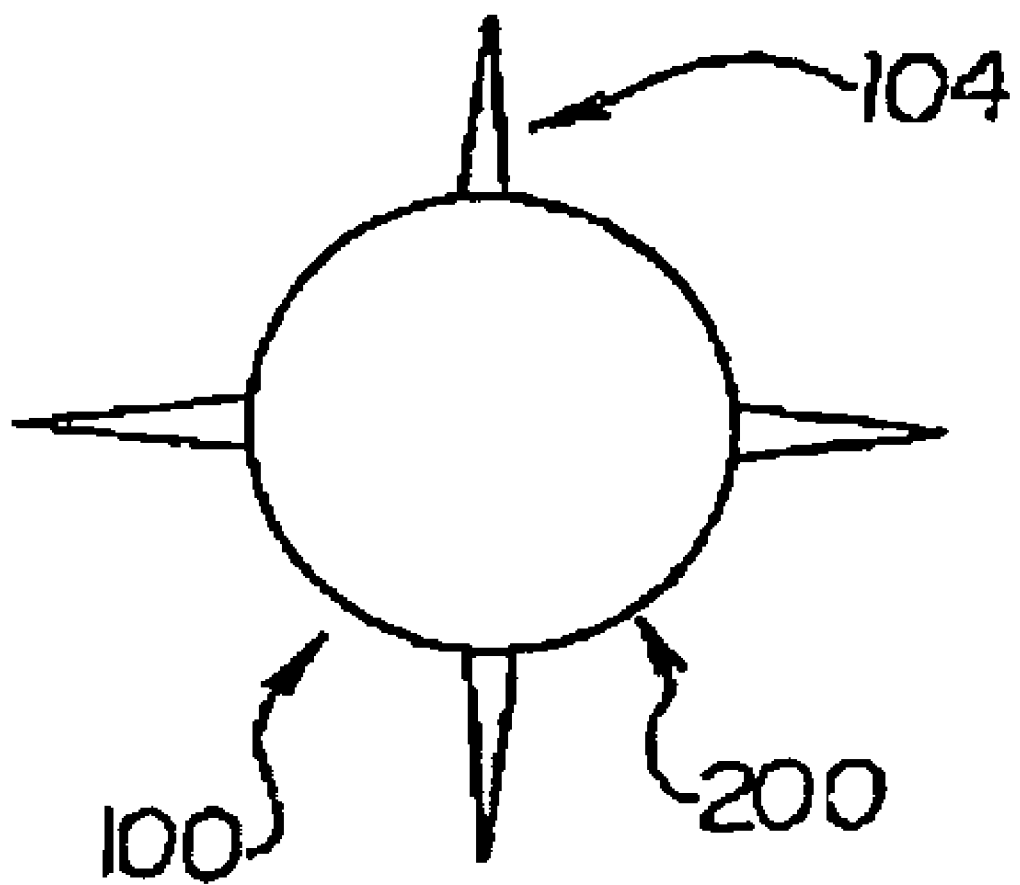

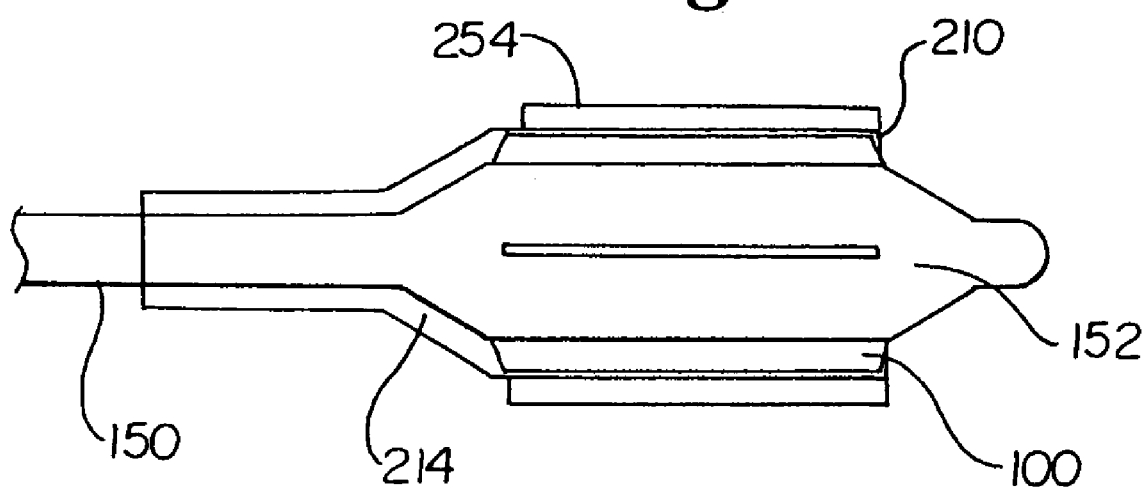

CUTTING STENT AND BALLOON

BACKGROUND OF THE INVENTION

The blockage of human arteries can lead to a variety of serious medical complications. This is so because arterial blockages reduce blood flow through the affected artery and may result in damage to the tissue that is relying on the blood supply. For example, if the blockage is in an artery which supplies blood to the heart itself, a heart attack may result.

Such arterial blockages, which are also called stenoses, are typically caused by the build-up of atherosclerotic plaque on the inside wall of an artery. In fact, several such stenoses may occur contiguously within a single artery. This can result in a partial, or even complete, blockage of the artery. As a result of the danger associated with such a blockage, several methods and procedures have been developed to treat stenoses. One such method is an angioplasty procedure which uses an inflatable balloon to dilate the blocked artery. A typical inflatable angioplasty device, for example, is disclosed in U.S. Pat. No. 4,896,669.

Angioplasty balloons have enjoyed widespread acceptance in the treatment of stenoses. Recent studies, however, have indicated that the efficacy of the dilation of a stenosis is enhanced by first, or simultaneously, incising the material that is creating the stenosis. Consequently, recent developments have been made to equip angioplasty balloons with cutting edges, or atherotomes, which are intended to incise a stenosis during the dilation procedure. For example, U.S. Pat. No. 5,196,024; U.S. Pat. No. 5,616,149 and U.S. Pat. No. 5,797,935 respectively describe an inflatable angioplasty balloon having a number of atherotomes mounted longitudinally on the surface of the balloon. Upon inflation of the balloon, the atherotomes induce a series of longitudinal cuts into the surface of the stenotic material as the balloon expands to dilate the stenosis. As a result of such cuts, the stenosis is more easily flattened, and the likelihood of damaging the artery during dilation is reduced.

It would be desirable to provide a stent and balloon combination which allows for controlled dissection of the cutting balloon and which allows for the deployment of a stent without having to first withdraw the cutting balloon. It would also be desirable to provide for a system including a cutting stent as well.

In addition to the above, it would be desirable to provide a method and apparatus for readily providing an existing balloon with cutting blades.

All US patents and all other published documents mentioned anywhere in this application are incorporated herein by reference in their entirety.

Without limiting the scope of the invention, a brief summary of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well for the purposes of complying with 37 C.F.R. 1.72.

BRIEF SUMMARY OF THE INVENTION

The present invention is directed to several embodiments. In at least one embodiment the invention is directed to an implantable and expandable medical device such as a stent which is equipped with a cutting blade.

In at least one embodiment, the invention is directed to a catheter having an inflatable member such as a medical balloon mounted thereon. In some embodiments the medical balloon may be equipped with at least one cutting blade. The medical balloon may be utilized with a stent or other implantable medical device, wherein one or more cutting blades of the balloon protrude through selected portions of the stent.

At least one embodiment of the invention is directed to a sheath or sleeve having at least one cutting blade mounted to the outer surface of the sheath. The sheath may be fitted on to an existing medical balloon to allow the balloon to act as a cutting balloon. In some embodiments a sheath equipped balloon may be used to deliver or seat a stent into a body lumen.

In at least one embodiment a blade equipped sheath may be disposed about a stent prior to stent delivery.

Additional details and/or embodiments of the invention are discussed below.

BRIEF DESCRIPTION OF THE DRAWINGS

A detailed description of the invention is hereafter described with specific reference being made to the following drawings.

FIG. 3 is a perspective view of an embodiment of the invention.

FIGS. 4-6 are end views of inventive stents with three, four and eight blades, respectively.

FIG. 32 is a side elevational view of an embodiment of the invention wherein the sheath is disposed about a portion of a stent which is disposed about a portion of a balloon catheter.

DETAILED DESCRIPTION OF THE INVENTION

Figure 1:
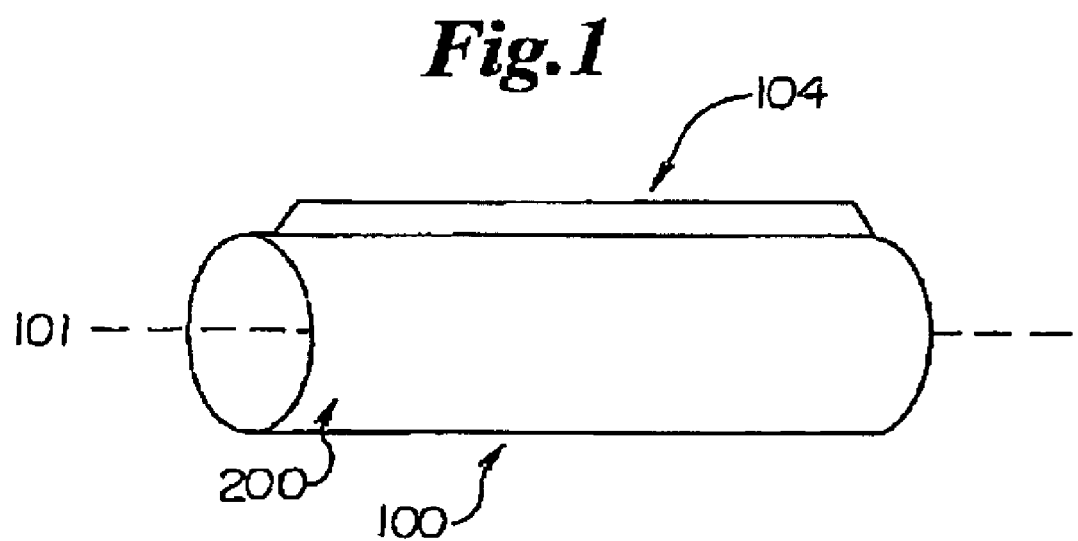
FIG. 1 is a perspective view of an embodiment of the invention wherein a stent is shown with a substantially longitudinally oriented cutting blade thereon.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 2:
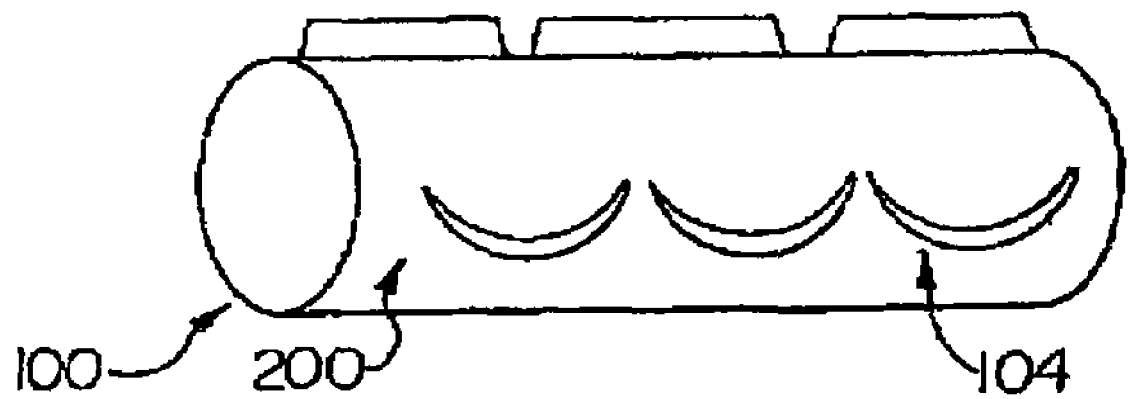
FIG. 2 is a perspective view of an embodiment of the invention.
Figure 3A:
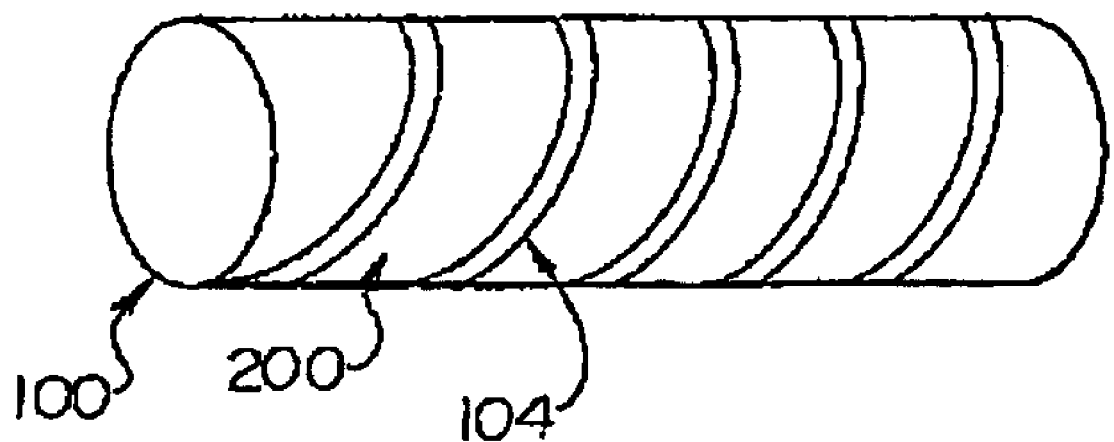
FIG. 3a is a perspective view of an embodiment of the invention.

In one embodiment, the invention is directed to a stent for implantation in the body. A stent, shown generally at 100 in FIG. 1, has an inner surface and an outer surface. The outer surface comprises at least one cutting blade 104 and typically a plurality of cutting blades. In some embodiments the cutting blades are oriented parallel to a longitudinal axis 101 of the stent as shown in FIG. 1. In some cases however, the blades may be non-parallel to the longitudinal axis of the stent. For example, as shown in FIGS. 2 and 3, the blades may be curved or zig-zag shaped. In at least one embodiment, an example of which is shown in FIG. 3a, the stent 100 comprises a blade 104 that is spirally or helically disposed about the stent.

Figure 6:
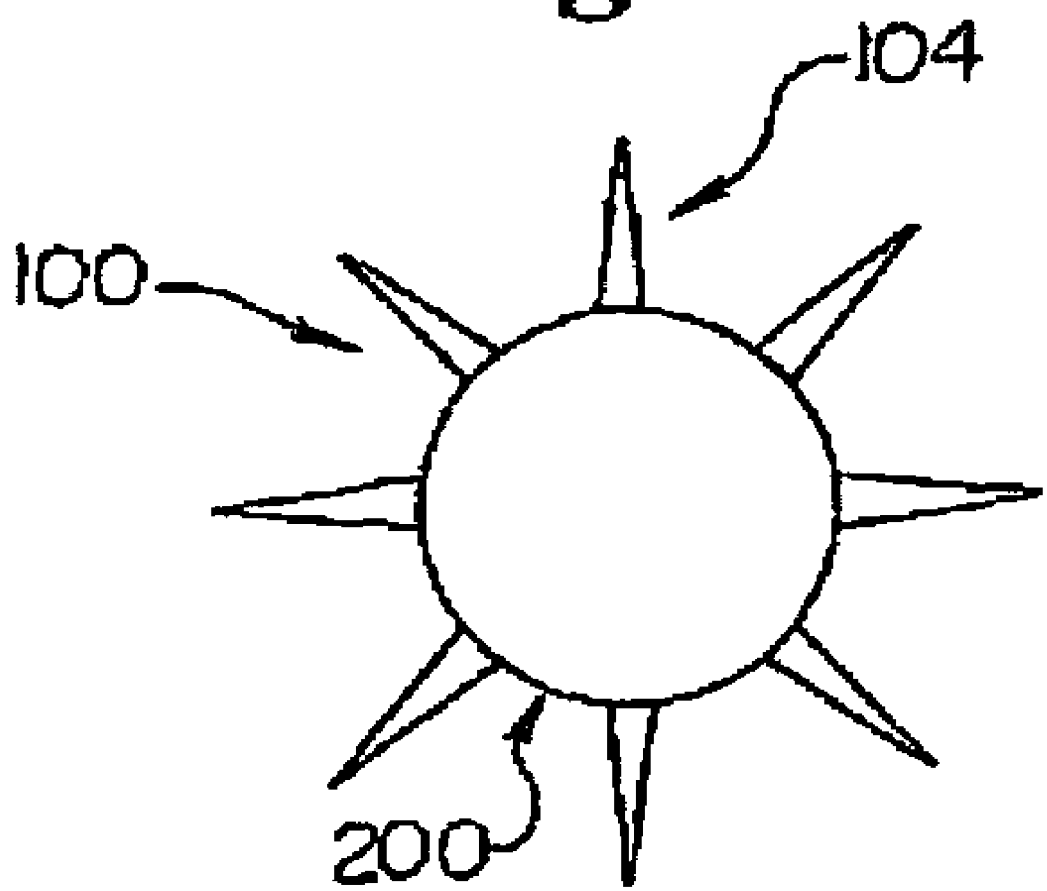

The stent of FIG. 1 has one blade. Stents with three, four blades and eight blades are shown in FIGS. 4-6 in end view. More generally, the inventive stents may have anywhere from one blade to twelve blades or more.

Figure 11:
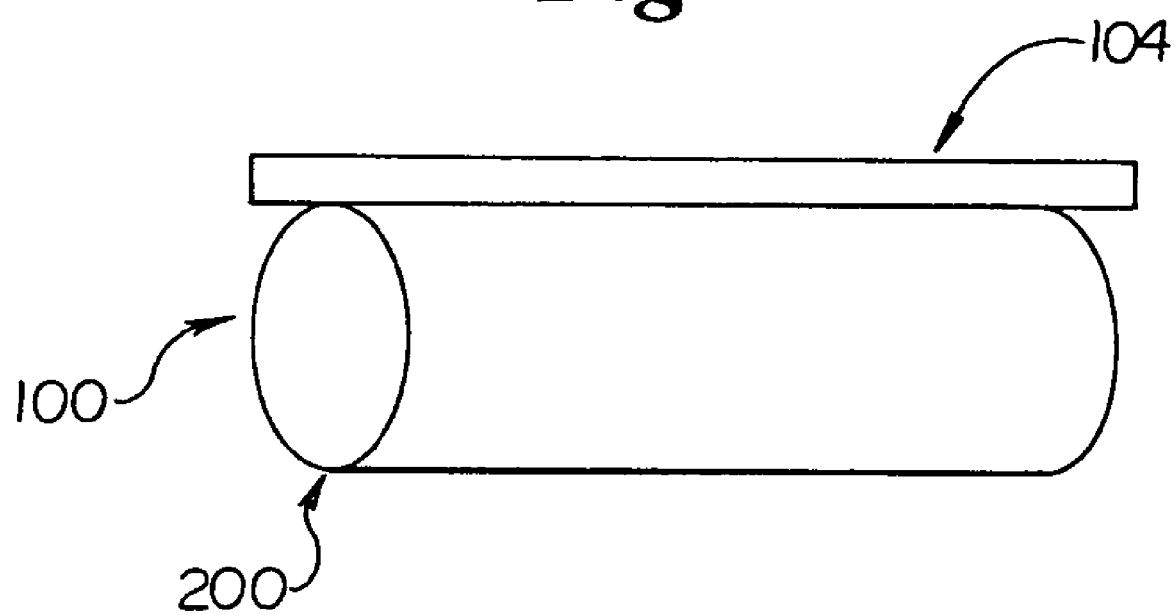
FIG. 11 is a perspective view of a stent with a longitudinal blade having a length greater than the stent body.

In some embodiments of the invention, the length of the cutting blade 104 is less than the length of the stent 100, such as is shown in FIG. 1. Alternatively, stent 100 may include one or more blades 104 that have a length greater than that of the stent body 200 such as is shown in FIG. 11.

Figure 7:
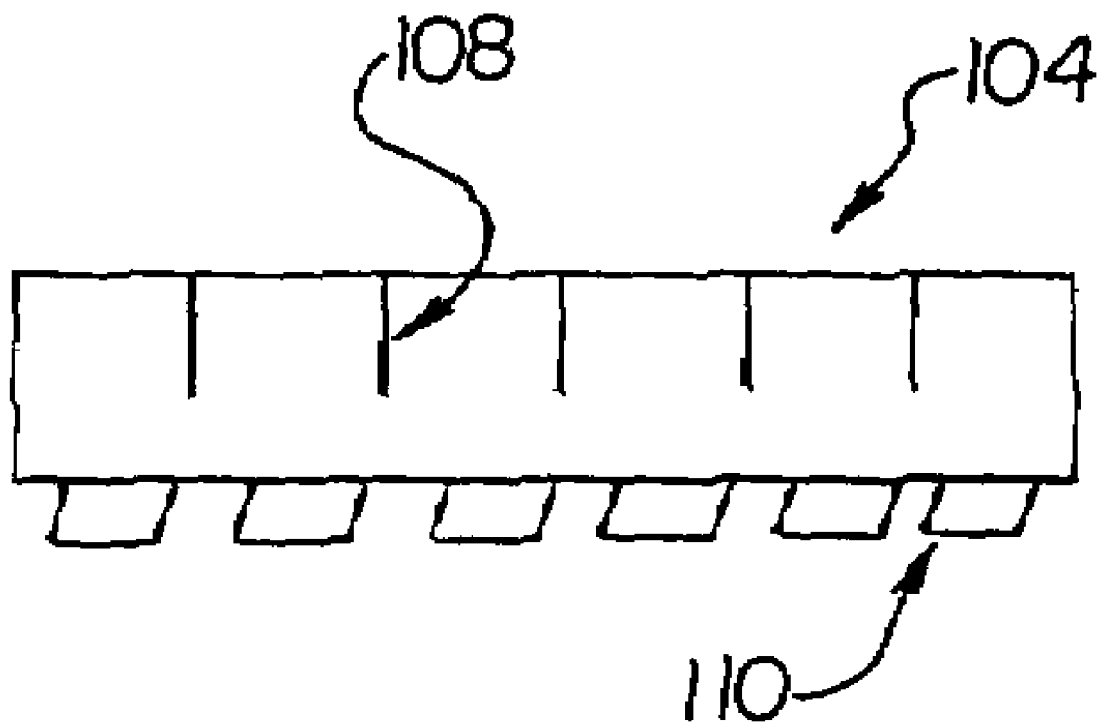
FIG. 7 is a side elevational view of a blade for use in the invention.

In some embodiments, the blade 104 desirably has a plurality of slots 108 therein to increase its flexibility, such as in the blade 104 shown in FIG. 7. The slots 108 defined by adjacent portions of the blade provide the blade 104 with desired flexibility.

Figure 8:
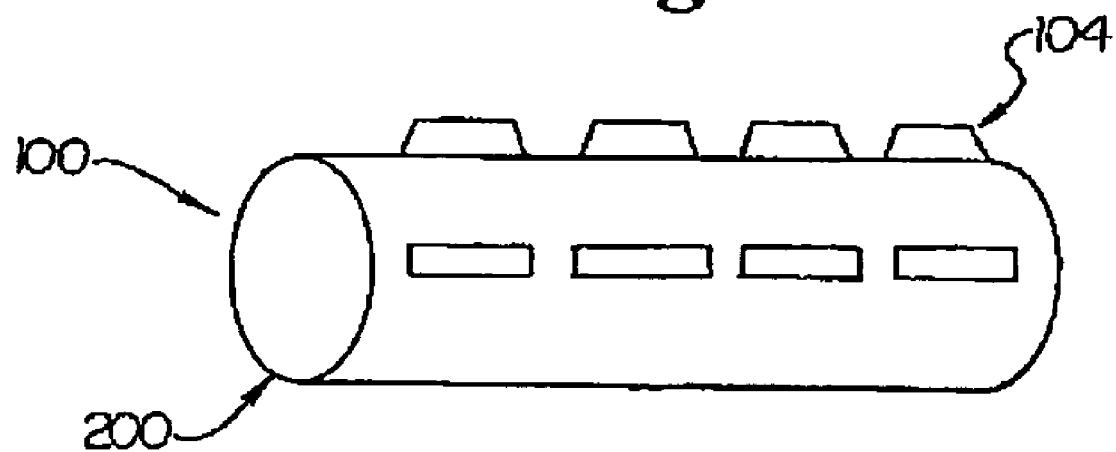
FIG. 8 is a side elevational view of a stent with a plurality of spot blades.

In some embodiments, such as for example the embodiment shown in FIG. 8, the length of an individual blade 104 is significantly less than the length of the stent body 200. In the embodiment shown in FIG. 8, stent 100 is provided with a plurality of spot blades 104 that are circumferentially aligned and longitudinally displaced from one another are provided.

Figure 12:
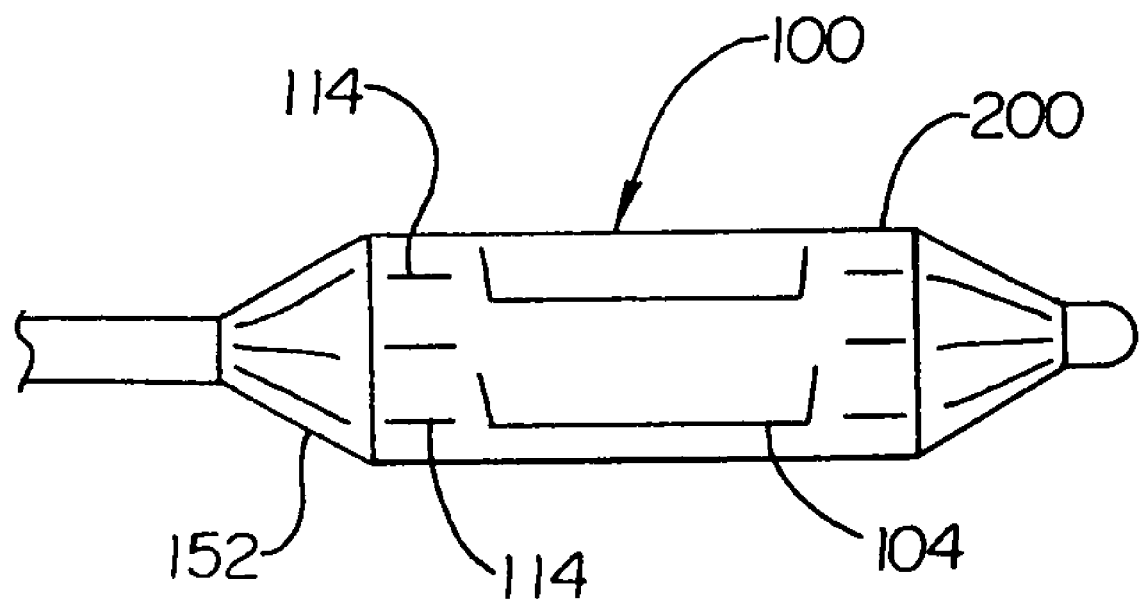
FIG. 12 is a side elevational view of a stent delivery catheter with an inventive stent shown thereon, the stent being shown in an unexpanded configuration with blades cut therein.

In the various embodiments described herein the cutting blade 104 may be formed of a different material from the stent 100 or of the same material as the stent. Such blade materials may include, but are not limited to metals, ceramics, glasses, polymers and any combinations or composites of thereof. In some embodiments of the invention, at least a portion of the stent 100, such as at least a portion of blades 104, may be at least partially constructed from one or more shape memory polymers, and/or shape memory metals such as nitinol, elgiloy, or others.

Where the blades 104 are made of a different material than the stent 100, the blades 104 may be affixed to the stent 100 via a suitable means including via the use of adhesives or via welding. For example, where the stent and blades are both made from metal, the blades may be welded to the stent.

Where the blades are made of the same material as the stent, the blades may be affixed to the stent using adhesives or welding as described above or may be formed by removing material from a stent preform during manufacture of the stent. An example of a stent whose blades are manufactured by removing material from the stent is shown in FIG. 12 mounted on a stent delivery balloon 152 prior to delivery. Stent 100 may include a plurality of cells 114 which have been formed by removing material from a tube or stent body 200. Cuts have also been made in the body 200 to fashion one or more blades 104.

The inventive stent of FIG. 12 is shown unexpanded with the blades in a closed state. In the closed state, the blades desirably extend substantially circumferentially about the stent body 200. The inventive stent of FIG. 12 is shown in an expanded configuration in FIG. 13. Blades 104 are shown in the open configuration extending radially outward from the stent body 200. Another inventive stent with blades cut therein is shown in an expanded configuration in FIG. 14. The stent of FIG. 14 differs from that of FIG. 13 in the placement of the cells relative to the blades.

Figure 21:
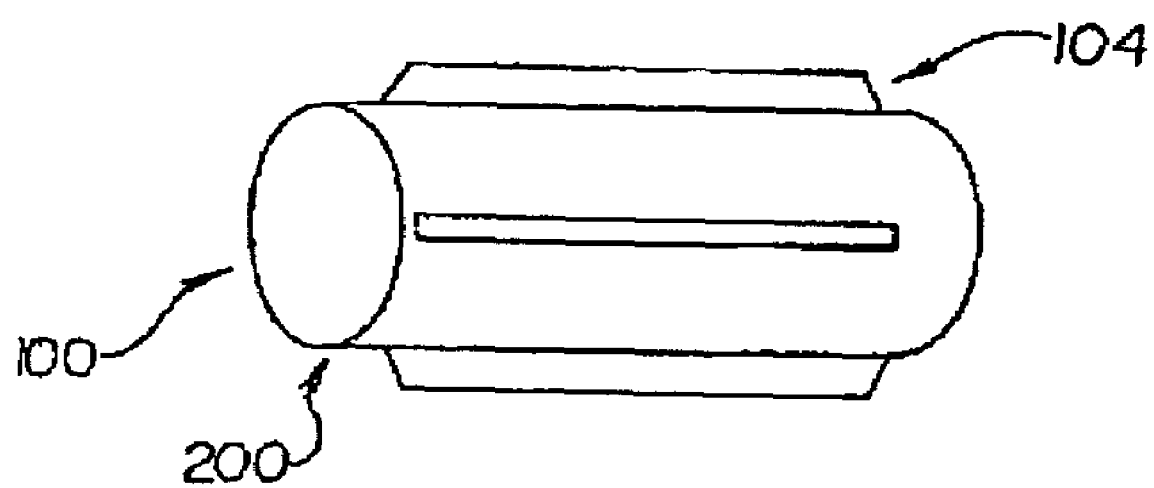
FIG. 21 is a side elevational view of an embodiment of the invention wherein the stent is shown in a first expansion state.
Figure 22:
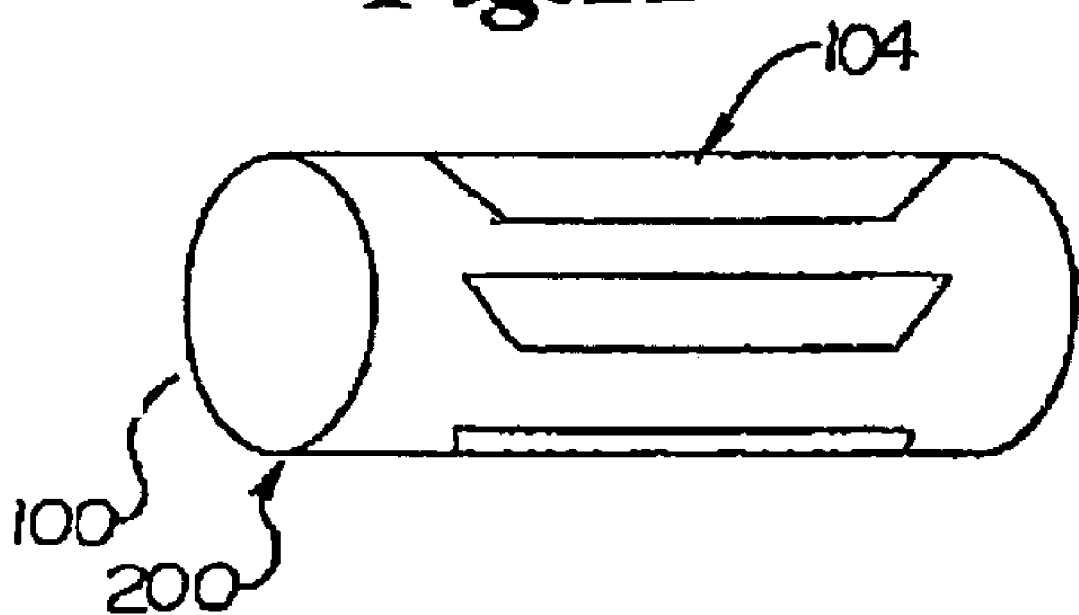
FIG. 22 is a side elevational view of the embodiment of the invention shown in FIG. 21 wherein the stent is shown in a second expanded state.

In at least one embodiment of the invention, shown in FIGS. 21-22, the stent 100 may have a variety of expansion states which may provide different deployment characteristics for blades 104. In FIG. 21, for example the stent 100 is shown in a first initially expanded state wherein the blades 104 are constructed and arranged to incise the stenosis. In the embodiment shown in FIG. 21, stent 100 is preferably in a partially expanded or a not yet fully expanded state. As the stent 100 is further expanded beyond the first inflation state shown in FIG. 21, the blades 104 are constructed to fold back down onto the stent 100 thereby preventing damage to the vessel wall when the stent 100 is fully expanded such as is shown in FIG. 22. Retraction of the blades 104 when the stent is fully expanded may be by a mechanical means such as the manner in which the blades are engaged to the stent, the use of a sheath or sleeve, the result of a preprogrammed shape memory, etc.

Blades 104 and/or 154 as described herein may be deployed and/or retracted by a variety of different mechanisms such as folding and unfolding the blade as described above, containing the blade within a valley or trough of the stent or balloon whereby when stent and/or balloon is expanded the blade is pushed out from the valley. In still other embodiments the blade may be deployed by any of a variety of mechanisms, but the blade subsequently is partially or completely biodegraded thereby avoiding any need to retract the blade. Mechanisms for deployment and/or retraction of a blade are also described in U.S. Pat. No. 5,320,634, U.S. Pat. No. 5,616,149 and U.S. Pat. No. 5,797,935 the entire content of each of which is incorporated herein by reference.

The cutting blades 104 of the various embodiments shown or described herein may be made of any suitable materials including stainless steel, cobalt nickel steel, ceramic materials, glass materials and biodegradable materials. It is also within the scope of the invention for the blades, or one or more portions thereof, to be radioactive. In embodiments where a radioactive blade is utilized, at least a portion of the blade may be constructed from or include a radioactive material or coating. In some embodiments at least a portion of the blade may be made radioactive by exposure to a radiation source.

As indicated above, in some embodiments a blade 104 may be at least partially constructed from one or more biodegradable materials. At a predetermined time following stent delivery, the blade 104 may be made to partially or totally degrade, thereby ensuring that blades 104 are not left imbedded in a vessel wall. In some embodiments where the blade 104 is wholly or partially degradable, the blade 104 may include a therapeutic agent which is delivered upon degradation of the blade 104. An example of a therapeutic agent is a drug such as paclitaxol.

Figure 10:
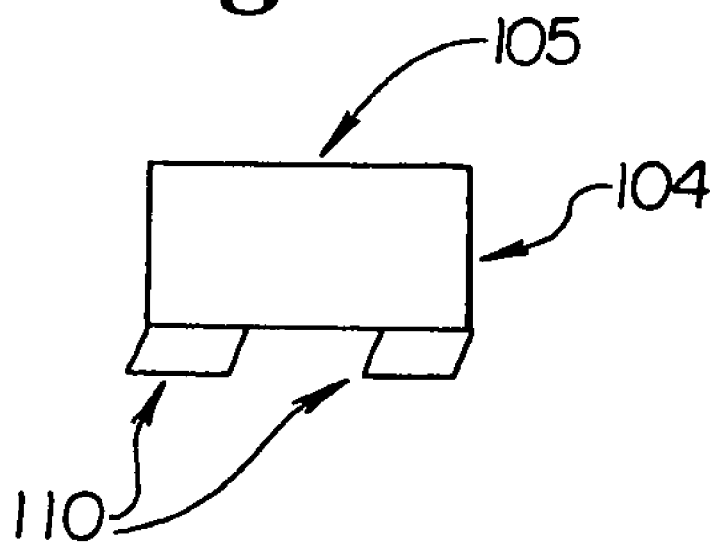
FIG. 10 is a side view of one of the spot blades of the stent of FIG. 8, showing the tabs.
Figure 13:
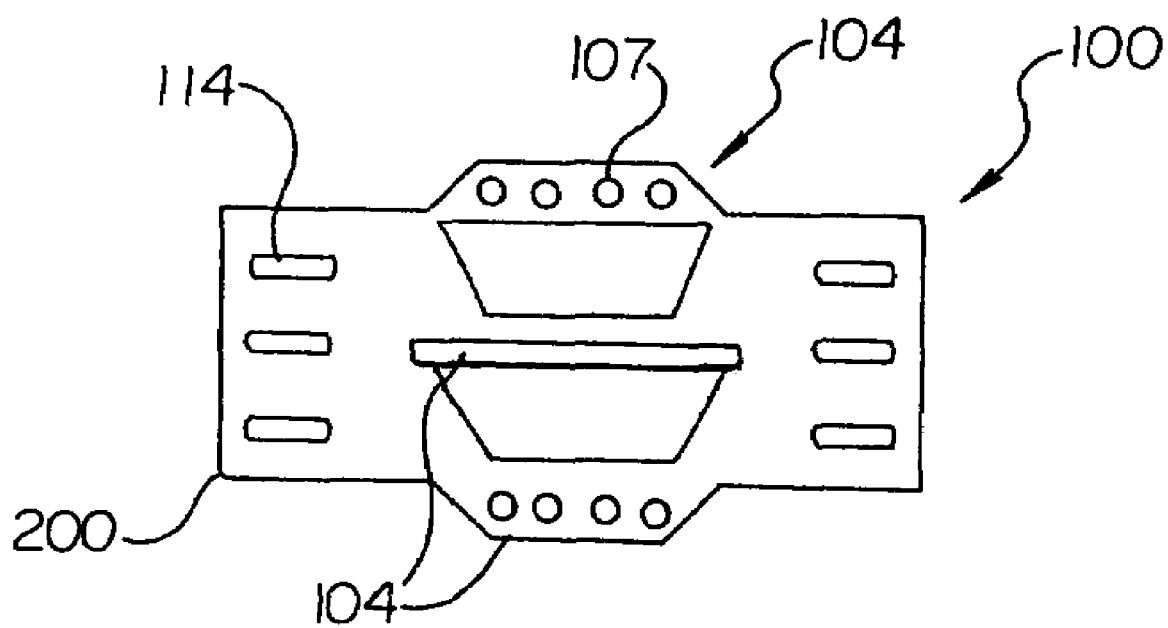
FIG. 13 is a side view of the inventive stent of FIG. 12 in an expanded configuration with blades cut therein.
Figure 14:
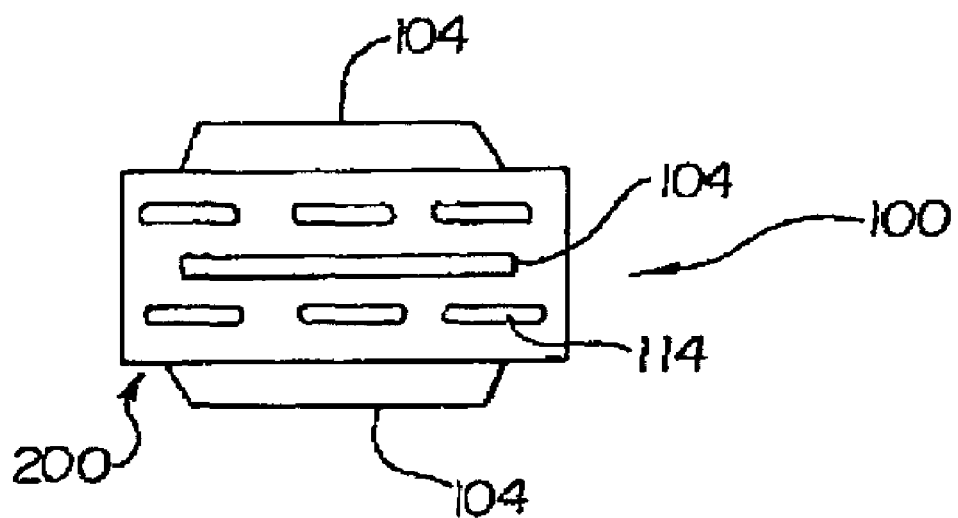
FIG. 14 is a side view of another inventive stent in an expanded configuration with blades cut therein.

In at least one embodiment, such as is shown in FIG. 10, at least a portion of the blade 104, such as the cutting edge 105 is coated with a biodegradable substance. The biodegradable substance may be or include a therapeutic substance, such as a drug that is delivered upon the degradation of the coating. In some embodiments the blade 104, such as is shown in FIG. 13, includes one or more pores or holes 107, which are constructed and arranged to contain one or more biodegradable drug carriers.

Figure 9:
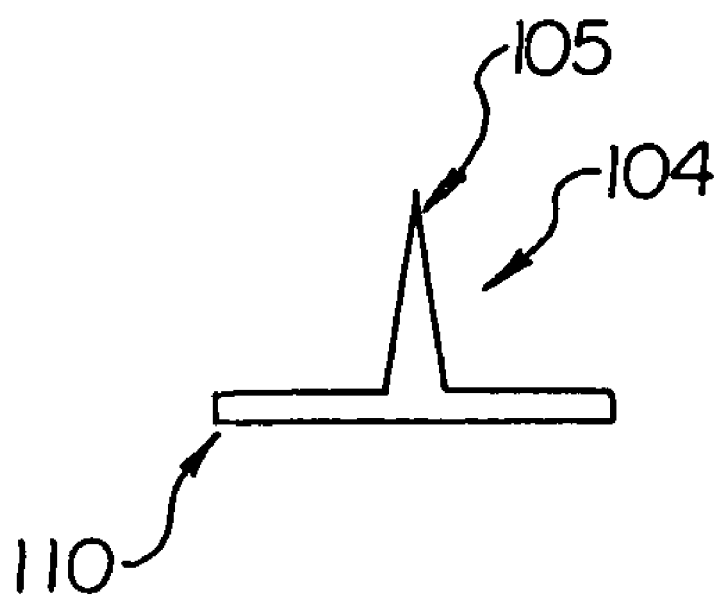
FIG. 9 is an end view of the blade of FIG. 7.

In at least one embodiment of the invention, the blades may be provided with tabs, shown at 110 in FIGS. 7 and 9-10, to facilitate welding or otherwise securing the blades to the stent. The tabs 110 may extend in perpendicular manner relative to the cutting edge 105 of the blade 104 as shown in the end view of FIG. 9. A desirable configuration of tabs 110 is shown for a spot blade 104, an example of which is shown in FIG. 10. Typically, the blades 104 will be folded down prior to deployment of the stent 100 and will open and extend circumferentially outward on deployment of the stent, either by self-expansion or balloon expansion. As indicated above, in some embodiments the blades 104 will fold back down about the stent body upon full expansion of the stent 100. Particular mechanisms for expansion and/or retraction of the blades 104 may vary.

As indicated above, in at least on embodiment of the invention the blades 104 may be at least partially constructed from a shape memory material, such as nitinol and/or one or more shape memory polymers. Blades 104 constructed from a shape memory material may be provided with a programmed shape such that at some point during the stent delivery process the blades 104 are configured to transition from the folded down state, such as is shown in FIG. 12, to the unfolded or circumferentially extended state shown in FIG. 13.

Figure 16:
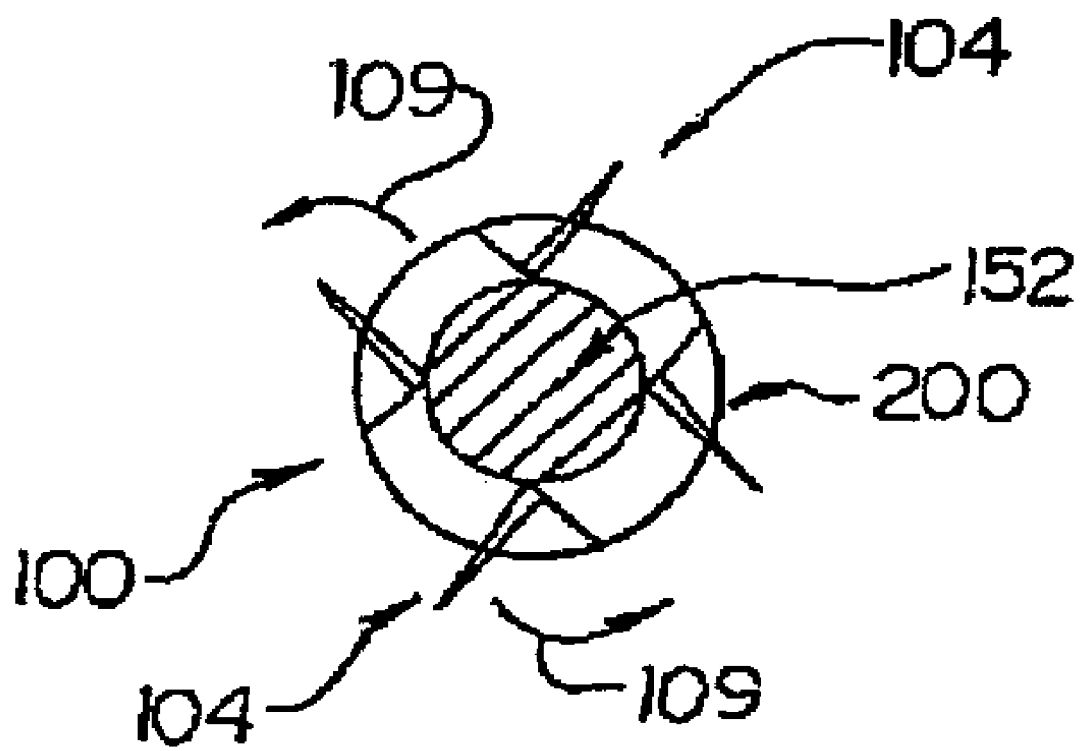
FIG. 16 is a cross-sectional view of an embodiment of the invention.

In an alternative embodiment, such as is shown in FIG. 16, the blades 104 are configured to include a bend 106. In the unexpanded state the blades 104 do not fully extend outward from the stent. As the stent 100 expands as a result of the inflation of a balloon 152 or other expansion devices, the blades 104 will rotate outward in a circumferential manner such as indicated by arrow 109 to attain a configuration such as is shown in FIG. 5 for example.

Figure 17:
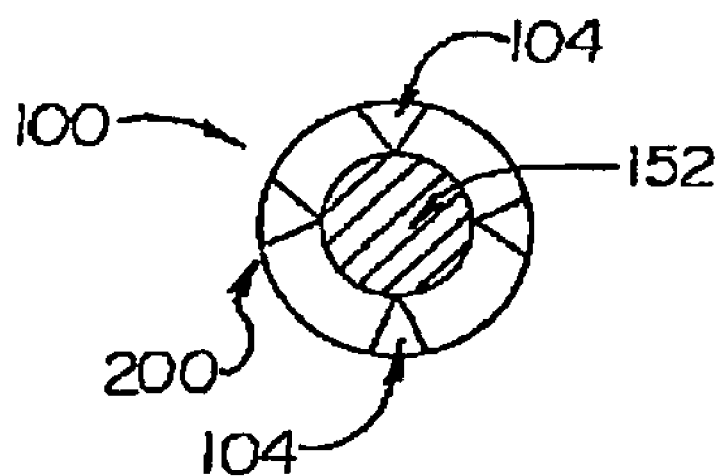
FIG. 17 is a cross-sectional view of an embodiment of the invention showing a stent in the unexpanded configuration mounted on a stent delivery balloon.
Figure 18:
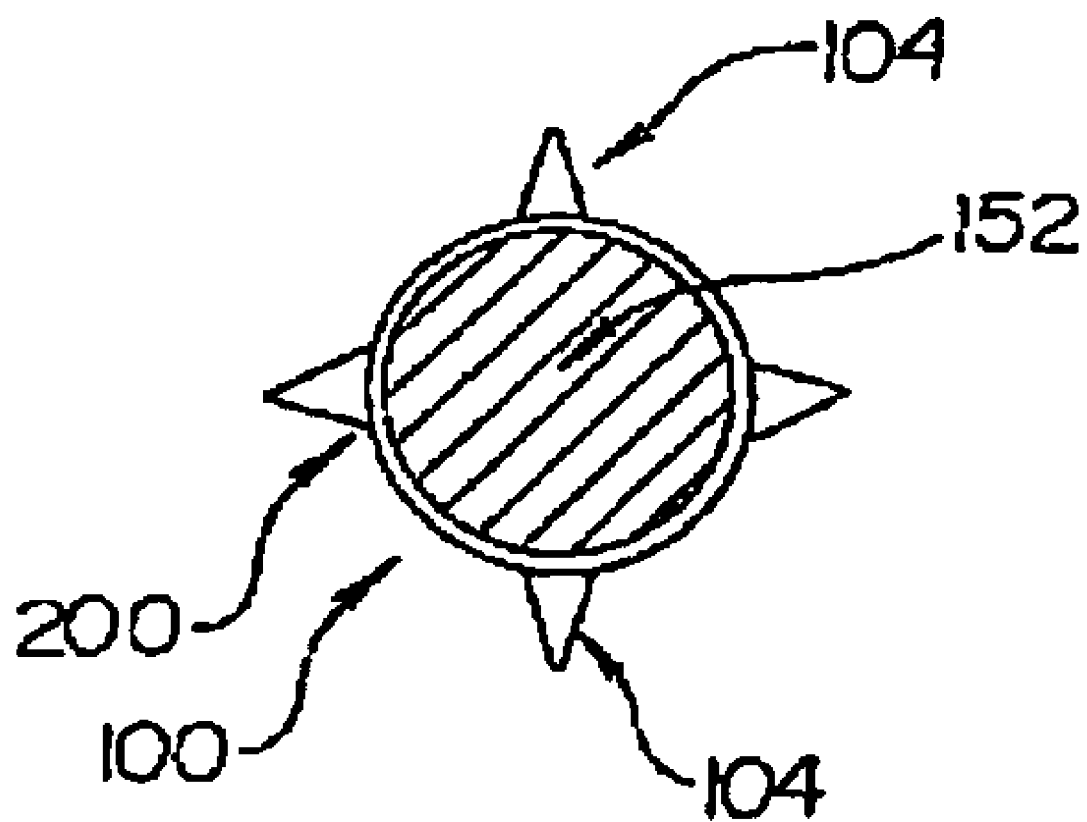
FIG. 18 is a cross-sectional view of the embodiment shown in FIG. 17 where the stent is shown in an expanded configuration.

In yet another embodiment shown in FIGS. 17 and 18, the blades 104 are configured to be generally V-shaped. When stent 100 is in the unexpanded state shown in FIG. 17, the blades 104 have a substantially inward pointing orientation shown. However, as the stent 100 is expanded, the blades 104 may be made to invert, thereby pointing radially outward from the stent 100, such as is shown in FIG. 18. Inversion of the V-shaped blades 104, may be the result of a shape memory action, a snap action resulting from the expansion of the stent 100 and/or balloon 152, or any other method desired.

Figure 20:
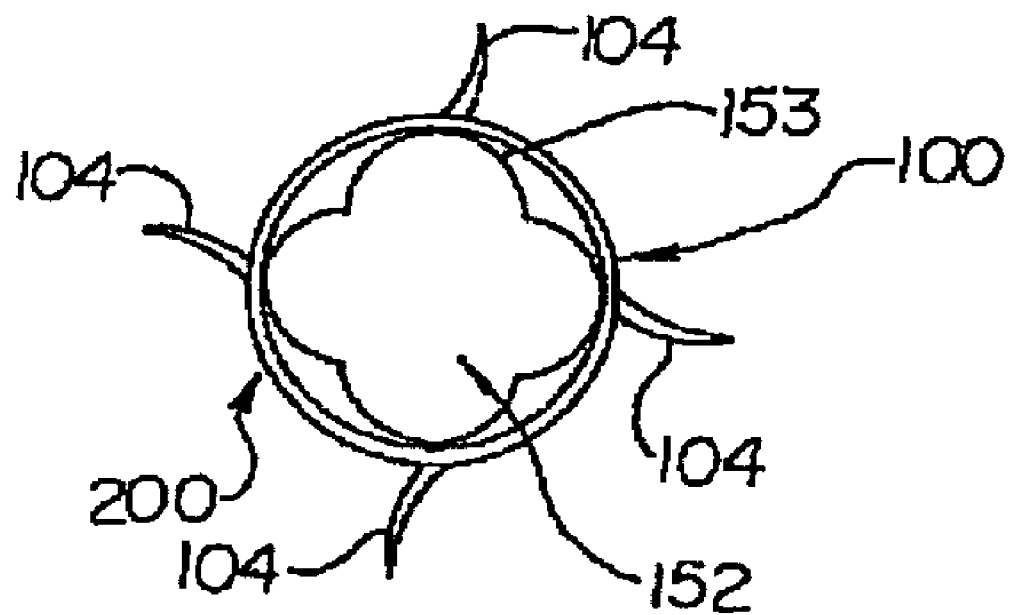
FIG. 20 is a cross-sectional view of an embodiment of the invention wherein a balloon having a plurality of bumps is positioned under a stent so that the bumps may aid in extending the blades of the stent.

As indicated above, some embodiments of the invention are also directed to the use of a balloon 152 for expansion and/or implantation of the stent 100. In some embodiments the shape of the balloon 152 may facilitate outward movement of the blades 104 from the stent 100 during expansion. For example, in the embodiment shown in FIG. 20 the balloon 152 includes a plurality of bumps 153 which are positioned underneath the portion of the blade 104 which extends radially inward relative to the stent 100, when the stent is in the unexpanded state as shown in FIGS. 12, 16 and 17. When the balloon 152 is expanded, the individual bumps 153 push on the inward projecting portions of the blades 104 thereby causing the blades 104 to extend in a radially outward manner relative to the stent 100.

Figure 25:
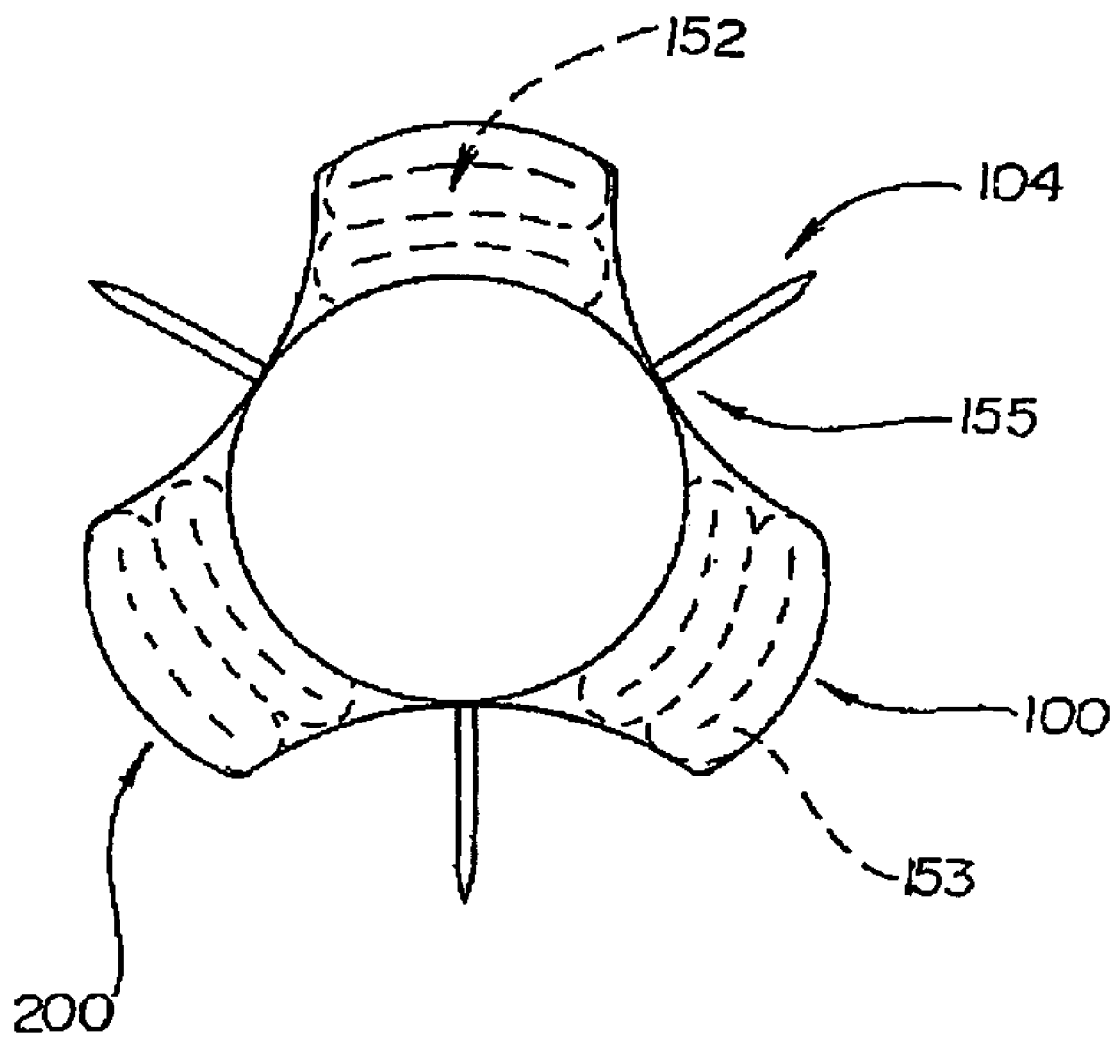
FIG. 25 is a cross-sectional view of an embodiment of the invention where a catheter having a balloon and stent are shown exaggerated to illustrate a potential relationship between the components.

In at least one embodiment of the invention, such as is shown in FIG. 25, the blades 104 of stent 100 are positioned in valleys 155 between the bumps 153. In some embodiments the bumps 153 are formed by folding portions of the balloon 152. The blades 104 are positioned between the bumps 153 within the valleys 155 that result from the formation of the bumps 153. In the unexpanded state shown, the blades 104 would be below the outer diameter of the balloon 152 as defined by the height of the bumps 153. During deployment of the stent 100, expansion of the balloon 152 will serve to drive the blades 104 outward from the valleys 155, and beyond the height of the bumps 153, to complete the cutting action.

Figure 15:
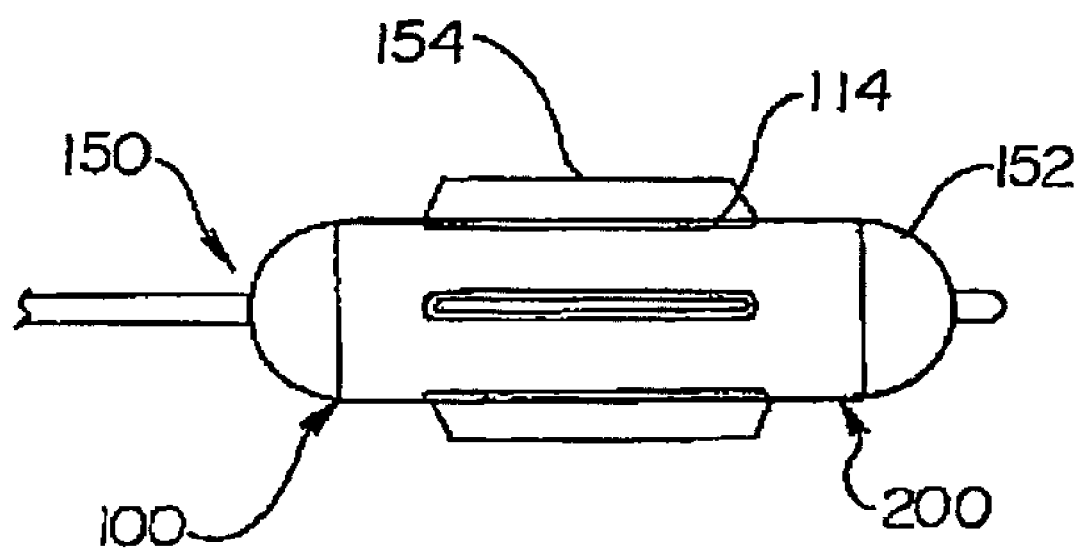
FIG. 15 is a side elevational view of a stent delivery catheter with an inventive stent shown thereon, the balloon is equipped with a plurality of balloon blades which are shown protruding through the stent.

In some embodiments of the invention, the balloon 152 may include one or more balloon blades 154 such as are shown in FIG. 15. Balloon 152 is associated with a catheter, shown generally at 150. The catheter 150 comprises a stent 100 and an inflatable medical balloon 152. Stent 100 is disposed about balloon 152 and defines a stent body 200 with a plurality of openings 114 therethrough. Cutting blades 154 optionally protrude through one or more of the openings 114 in the stent 100 upon expansion of the stent.

Figure 19:
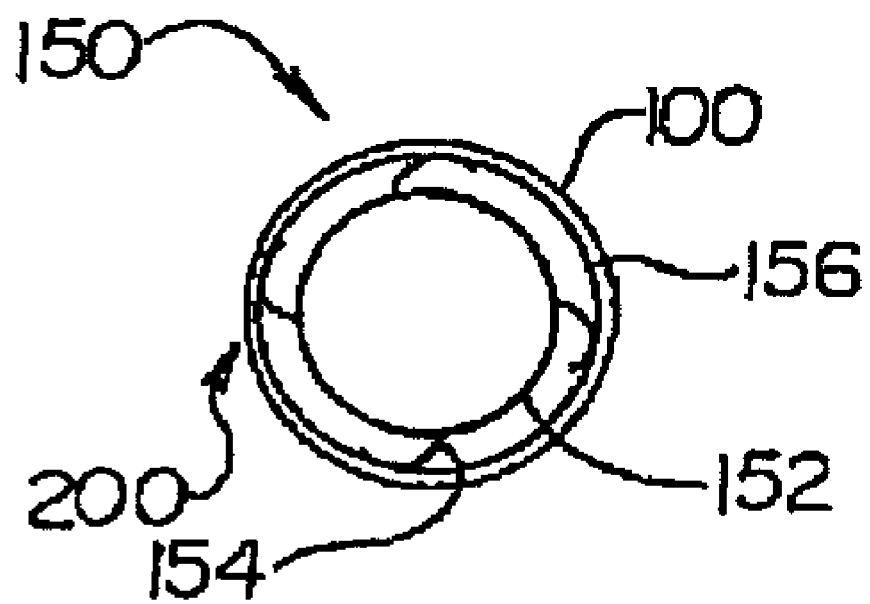
FIG. 19 is a cross-sectional view of an embodiment of the invention wherein a protective sheath is shown disposed between the balloon and stent.

In an embodiment of the invention shown in FIG. 19, the catheter 150 includes a retractable protective sheath 156 disposed between balloon 152 and stent 100. Sheath 156 may be used to prevent blades 154 from opening prematurely, for example, prior to the expansion of the stent.

As is shown in FIG. 15, in at least one embodiment, blades 154 may be sized to protrude through openings 114 in stent 100. In some embodiments, the blades 154 protrude through openings 114 after the balloon 152 is expanded to deliver stent 100. In some embodiments, after the stent 100 has been delivered, blades 154 retract when the balloon 152 is deflated prior to balloon withdrawal. In some embodiments, blades 154 may be sized to protrude through openings 114 in stent 100 before the stent has been expanded.

Figure 23:
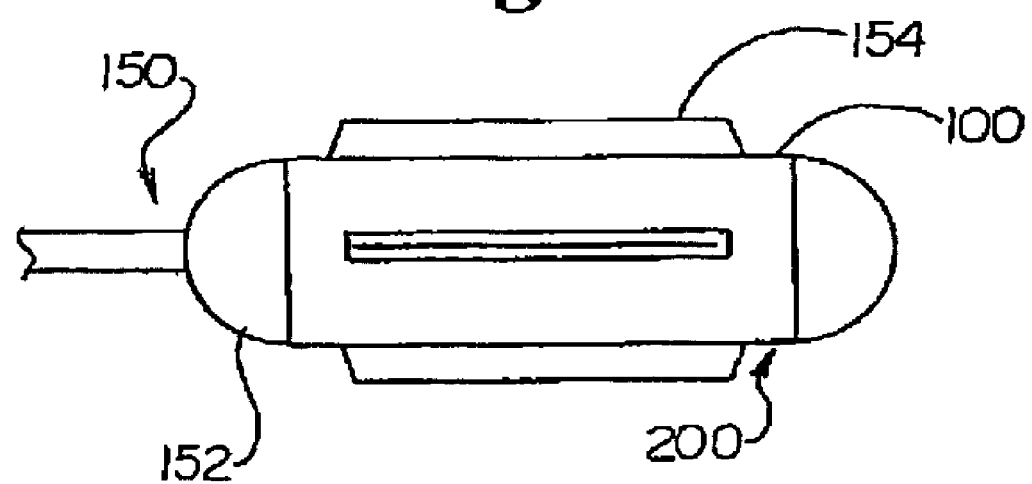
FIG. 23 is a side elevational view of an embodiment of the invention wherein a cutting balloon is shown dilated to a first inflated state.
Figure 24:
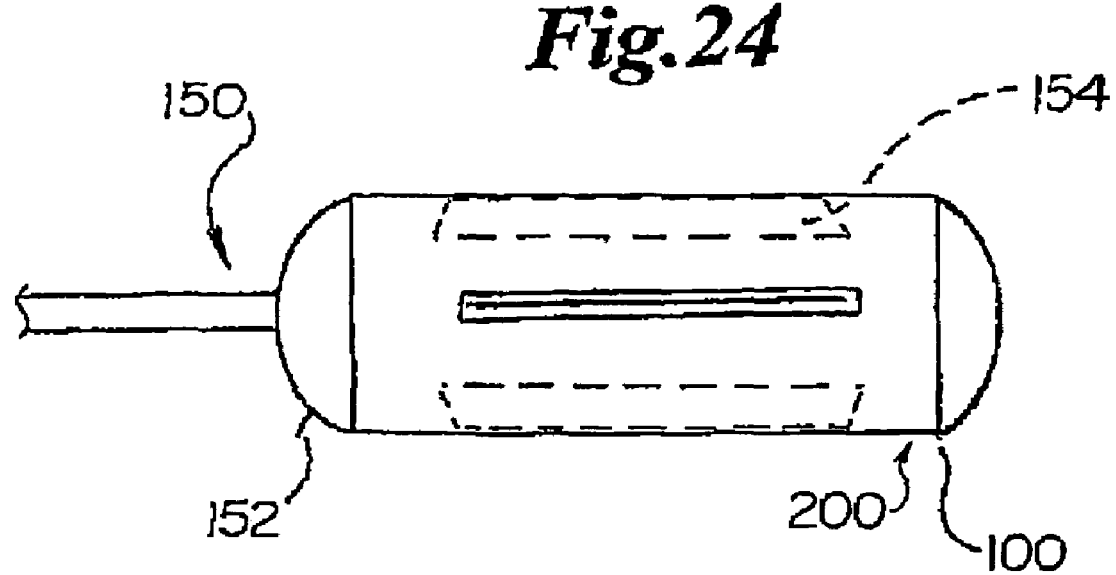
FIG. 24 is a side elevational view of the embodiment shown in FIG. 23, wherein the balloon is shown in a second inflation state.

In at least one embodiment, such as is shown in FIG. 23, when the balloon 152 is inflated to a first initially inflated state, blades 154 are constructed and arranged to protrude outwardly from the balloon. In some embodiments, such as is shown in FIG. 24 the balloon 152 may be inflated to an extent such that, the diameter of the balloon 152 is as great as or greater than the outwardly extending diameter of the blades 154. As a result, a stent 100 mounted on the balloon may be dilated beyond the diameter of the blades 154.

In the various embodiments shown and described herein that include a balloon 152, the cutting blades 154 used in conjunction with the balloon may be made of any suitable materials including stainless steel, cobalt nickel steel, ceramic materials, glass materials and biodegradable materials. It is also within the scope of the invention for the blades to be at least partially radioactive. In embodiments where a balloon blade is radioactive, at least a portion of the blade is constructed from or includes a radioactive material. In some embodiments, the balloon blade or a portion thereof is made radioactive by exposure to a radiation source.

Desirably, when a stent is used in conjunction with a cutting balloon, the stent will be designed to avoiding nicking or marring of the stent by the blades. The stent may have a scratch resistant inner surface by coating the inside surface of the stent with a biocompatible hemocompatible scratch resistant coating such as paralyene. Where the stent is constructed from one or more wires, the wire may be similarly coated. In some embodiments the entire stent is made scratch resistant relative to the blades by constructing the from a harder material than the blades. For example the stent, or a portion thereof, may be coated with paralyene, diamond-like coatings, etc.

In some embodiments the stent may be polished or coated with a lubricious material to allow the blades to slip relative to the stent body. In some embodiments of the invention the blades may be provided with a cover. In some embodiments the stent may be constructed so that the blades do not contact the stent. For example, in the embodiment shown in FIG. 15 the openings 114 may be sufficiently larger and wider than blades 154, to allow the blades 154 to pass therethrough without contact.

In some embodiments the balloon and stent assembly is constructed so that the blades require extra pressure to deploy during or after one or more of the stent and balloon are deployed. For example, the balloon may be constructed to contain stripes of material having a different compliance, thickness, or other material characteristic than the majority of balloon material. Some examples of balloons having such a hybrid construction are described in U.S. patent application Ser. No. 09/696,378, filed Oct. 25, 2000 and entitled Dimensionally Stable Balloons, the entire contents of which being incorporated herein by reference. The blade may be positioned on or within on a less compliant portion of the balloon. In such an embodiment, upon inflation of the balloon initially the stent will dilate at the areas of greater compliance around the balloon, i.e. the majority of the balloon's surface, finally the blades will be compelled to move up through the stent when a predetermined pressure is reached.

In another embodiment, the balloon material may be provided with a variable compliance. In this embodiment the blades rest upon the balloon as it is inflated. As the balloon opens symmetrically, at a predetermined pressure, the balloon's compliance changes and causes the blades to open up and move through the stent.

In yet another embodiment the balloon includes a coating, sheath, wrapping, adhesive, etc. that retains the blades down against the balloon. As the balloon dilates, it will not release the blades until a predetermined diameter, pressure, etc. is reached.

Figure 26:
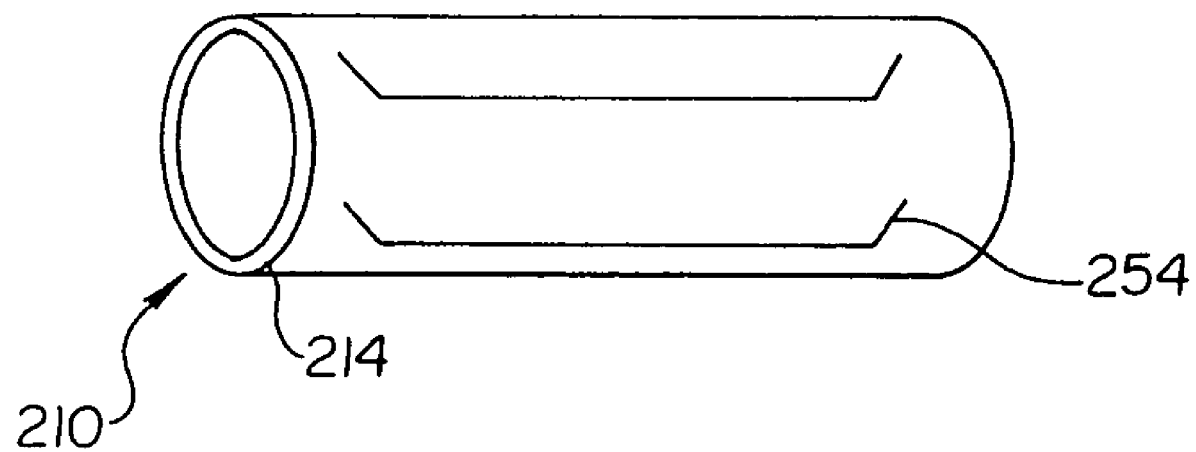
FIG. 26 is a perspective view of an embodiment of the invention comprising a sleeve.

In another embodiment of the invention shown in FIG. 26, a flexible tubular member or sheath 210 is shown. Sheath 210 is a unique type of sheath having one or more sheath blades 254 mounted externally on the tubular body 214. In some embodiments at least a portion of the sheath is constructed from at least on polymeric material. The tubular body 214 of the sheath and the blades 254 may be of the same or different material.

Blades 254 may be positioned or oriented in any manner desired about the sheath body 214. Sheath 210 may be configured to act as a pull back sheath, or act as a leave-in-place member disposed about a stent or balloon to provide the stent or balloon with a temporary or permanent bladed surface.

Figure 27:
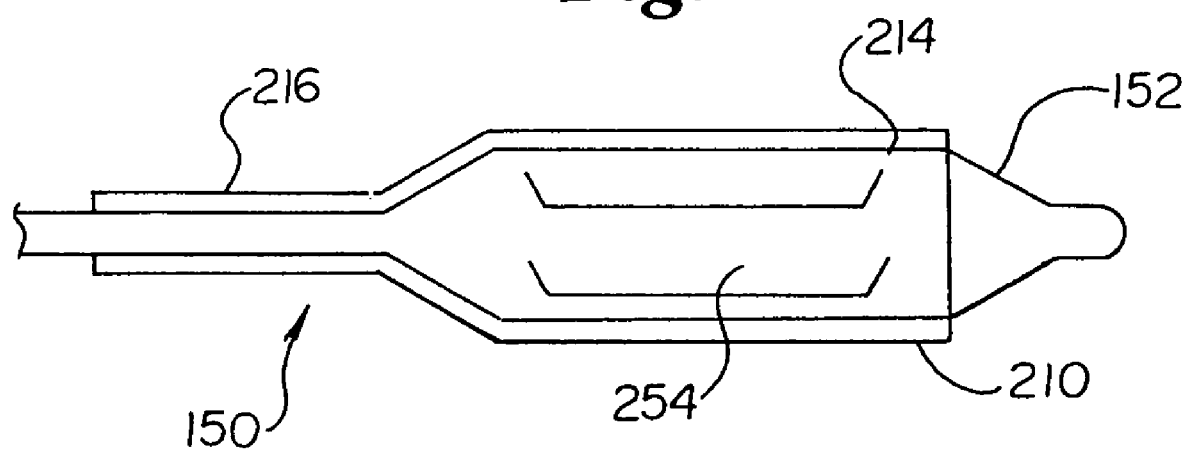
FIG. 27 is a side elevational view of the embodiment shown in FIG. 26 disposed about a portion of a balloon catheter.

In the embodiment shown in FIG. 27, sheath 210 is shown fitted over an existing dilatation balloon 152 of a catheter 150. The body 214 of the sheath may be of any length desired, and in some embodiments may extend over all or a portion of the length of the catheter 150. The proximal portion of the sheath 216 may extend toward the proximal end of the catheter 150 and may act as a pull back member for retracting the sheath 210 off of the balloon 152 at any time.

Figure 28:
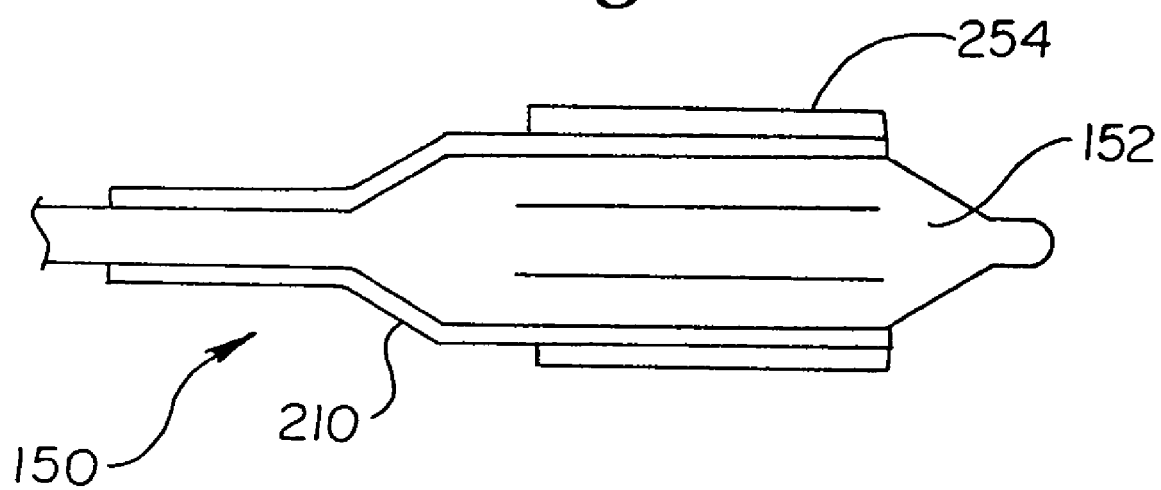
FIG. 28 is a side elevational view of the embodiment shown in FIG. 27, wherein the sleeve is shown in an expanded diameter configuration.

When used on a balloon 152, the blades 254 may be configured to extend outward from the body 214 when the balloon 152 is expanded such as in the manner shown in FIG. 28. In some embodiments, when the balloon 152 is deflated the sheath 210 contracts in diameter about the balloon 152. As the sheath 210 is contracted the blades 254 contract inward about the catheter 150 and/or fold back down about the sheath 210.

In some embodiments, the blades 254 may be configured with a variety of expansion and/or retraction mechanisms. For example, where the blades are at least partially constructed from a shape memory material, the blades 254 may be made to expand outward from the sheath body 214 according to a pre-programmed memory.

In some embodiments of the invention, the sheath 210 employs one or more mechanisms to prevent the blades 254 from prematurely moving or extending from a folded down configuration, such as is shown in FIG. 27, to the expanded configuration shown in FIG. 28. Some examples of mechanisms that may be used to retain the blades in the unexpanded configuration include the use one or more retractable sheaths, sleeves or socks placed over the bladed sheath 210 and then retracted to allow the blades 254 to expand; the use of a chemical adhesive between the sheath body 214 and the blades 254; the use of biodegradable bands, ties, or other securement devices that upon degradation the blades 254 would be free to expand; etc.

Figure 29:
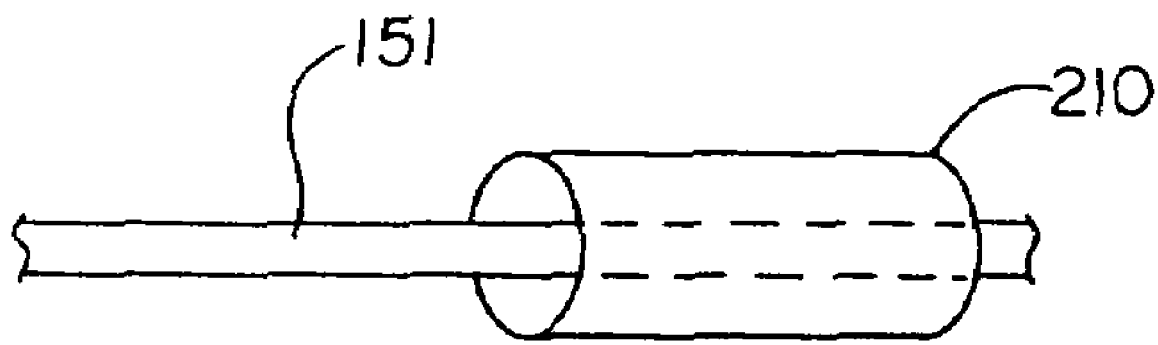
FIG. 29 is a perspective view of an embodiment of the invention shown in FIG. 26 wherein the sleeve is shown disposed about a portion of a catheter.
Figure 30:
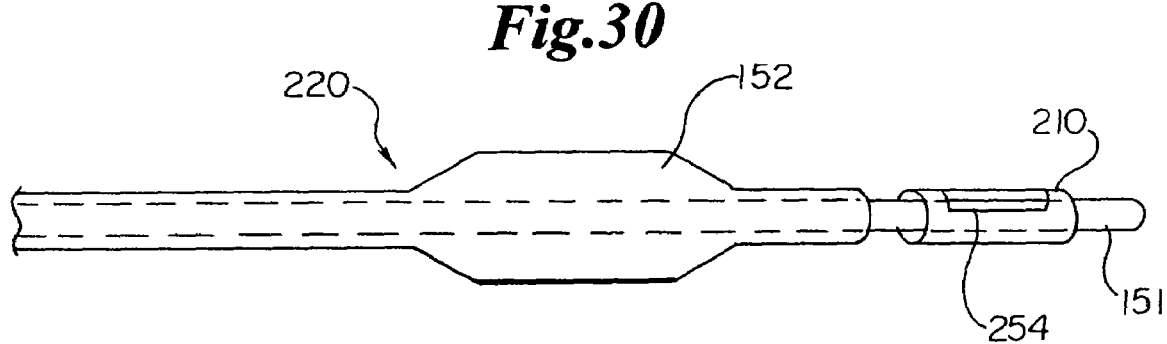
FIG. 30 is a perspective view of the embodiment shown in FIG. 29 shown in conjunction with a catheter assembly.

In some embodiments of the invention, such as in the embodiment shown in FIG. 29, the sheath 210 is disposed about a catheter member 151, such as a guide wire or other narrow elongate member. Such a catheter member 151 may be used with other existing catheter assemblies. For example, if mounted on a guide wire of an existing assembly 220, such as is shown in FIG. 30, the sheath 210 may be advanced directly through the existing catheter assembly 220 to the stenosis site. The blades 254 may then be expanded prior to or subsequent to dilatation of the balloon 152.

Figure 31:
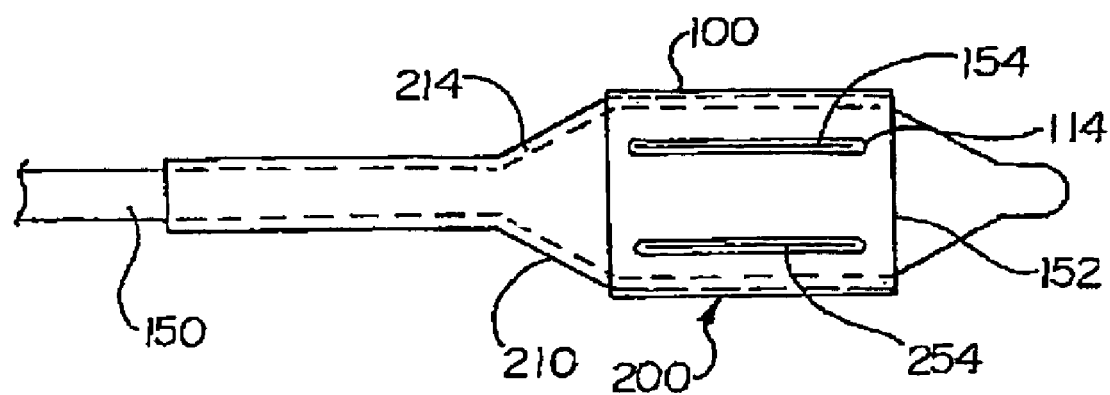
FIG. 31 is a side elevational view of an embodiment of the invention wherein the sheath is disposed about a portion of a balloon catheter and a stent is disposed about at least a portion of the sheath.

In some embodiments, such as for example the embodiment shown in FIG. 31, the sheath 210 is disposed about a portion of a balloon 152, or other portion of a catheter assembly 150, a stent 100 however may be disposed about the sheath 210, to allow blades 254 to extend through openings 114 defined by the stent 100 when the blades 254 are expanded in the various manners described above. In some embodiments, the blades 254 may be designed to move or expand to the expanded configuration prior to or during expansion of the stent 100.

Alternatively, a stent 100 may be effectively provided with one or more blades 254 by disposing sheath 210 over the stent 100 such as is shown in FIG. 32. In some embodiments the sheath 210 may act to retain the stent in the unexpanded state. At a desired time the sheath 210 is retracted off of the stent 100, thereby allowing the stent to be expanded and delivered. In some embodiments the blades 254 may be placed in the expanded configuration and back to the folded configuration prior to retraction of the sheath 210 and delivery of the stent 100. Blades 254 may be expanded and subsequently folded by a shape memory mechanism, by partial inflation and deflation of a balloon underlying the stent 100 (if present), or other mechanisms as are know.

In some embodiments the blades 254 and/or sheath body 214 may be fully biodegradable thereby allowing the sheath 210 to be left on the stent 100 during delivery of the stent 100. The sheath 210 will then degrade at a predetermined time during or subsequent to stent implantation.

In the various embodiments described herein, the blades may be made to open up at a desired stent diameter.

Any portion of the inventive stents, sheaths, balloons and inventive catheters described herein may optionally be provided with any of the coatings described below. In one embodiment of the invention, only the blades, whether on the stent or balloon, are provided with a coating.

The coating may comprise one or more non-genetic therapeutic agents, genetic materials and cells and combinations thereof as well as other polymeric coatings.

Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vasoactive mechanisms.

Genetic materials include anti-sense DNA and RNA, DNA coding for, anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor, cell cycle inhibitors including CD inhibitors, thymidine kinase ("TK") and other agents useful for interfering with cell proliferation the family of bone morphogenic proteins ("BMP's"), BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Desirable BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Cells can be of human origin (autologous or allogeneic) or from an animal source (xenogeneic), genetically engineered if desired to deliver proteins of interest at the transplant site. The cells may be provided in a delivery media. The delivery media may be formulated as needed to maintain cell function and viability.

Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL®), fibrin, collagen and derivatives thereof, polysaccharides such as celluloses, starches, dextrans, alginates and derivatives, hyaluronic acid, squalene emulsions. Polyacrylic acid, available as HYDROPLUS® (Boston Scientific Corporation, Natick, Mass.), and described in U.S. Pat. No. 5,091,205, the disclosure of which is hereby incorporated herein by reference, is particularly desirable. Even more desirable is a copolymer of polylactic acid and polycaprolactone.

The inventive stents disclosed herein may be of substantially uniform diameter or of non-uniform diameter. For example, the inventive stent may taper in the expanded state. This may be accomplished, for example, where the stent comprises serpentine bands, by decreasing the amplitude of the serpentine bands from one end of the stent to the other, or just along a desired portion of the stent. A tapered portion may be provided anywhere along the stent. For example, half of the stent, starting at one end of the stent, may be provided with a taper. Another way to achieve a tapered expanded stent is to change the stiffness of the serpentine bands and/or any connectors which extend between serpentine bands such that the stiffness of the serpentine bands and/or the connectors varies along the length of the stent. The stiffness of the various portions of the stent may be changed by altering length, width or thickness, adding additional stiffening material, using a chemical or mechanical means to alter the physical properties of the stent material, or applying one or a series of elastic elements about the stent.

Stent as described herein may be fabricated using a variety of potential fabrication methods, including but not limited to: laser etching, chemical etching, photo etching, weaving, knitting, tying, chemical or vapor deposition, molding, dipping, welding connecting, etc.

The inventive stents may be used in arteries and vessels including coronary vasculature, the esophagus, the trachea, the colon, the biliary tract, the urinary tract, the prostate, the brain, urethras, fallopian tubes, and bronchial tubes.

Typically, the inventive stents will be delivered via a stent delivery catheter with an expandable member such as a balloon. Desirably, the catheter will include a deployment sheath disposed about the stent. Suitable catheters for use with the inventive stents are known in the art.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

The particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

We claim:

1. A catheter for delivering a stent comprising a stent, an inflatable medical balloon, and a retractable expandable sheath disposed between the balloon and the stent, the inflatable medical balloon comprising a plurality of cutting blades, the stent having a sidewall with a plurality of openings therethrough, the stent disposed about the balloon wherein each cutting blade extends through the at least one of the plurality of openings in the stent; wherein the sheath prevents the cutting blades from opening; and wherein the cutting blades are sized to protrude through the openings in the stent after the stent has been expanded and after the sheath has been retracted.

2. The catheter of claim 1 wherein the at least one cutting blade comprises a biodegradable polymer.

3. The catheter of claim 1 wherein the at least one cutting blade is at least partially constructed from at least one member of the group consisting of: polymers, ceramic, glass, metal, and any combinations thereof.

4. The catheter of claim 1 wherein medical balloon has a first expansion state and a second expansion state, when the balloon is expanded to the first expansion state the at least one cutting blade radially expands from the balloon, in the second expansion state the stent is expanded beyond the at least one cutting blade.

* * * * *